United States Patent [19]
Gallop

[11] Patent Number: 6,057,465
[45] Date of Patent: May 2, 2000

[54] ARENE-TRANSITION METAL LINKERS FOR SOLID PHASE SYNTHESIS

[75] Inventor: Mark A. Gallop, Los Altos, Calif.

[73] Assignee: Glaxo Wellcome Inc., Research Triangle Park, N.C.

[21] Appl. No.: 08/861,954

[22] Filed: May 22, 1997

[51] Int. Cl.⁷ .............................. C07F 11/00; C07F 15/00
[52] U.S. Cl. ................. 556/11; 556/20; 556/46; 556/47; 556/58; 556/59; 556/136; 556/140; 556/141; 556/142; 787/2; 787/3
[58] Field of Search ................... 556/11, 20, 46, 556/47, 58, 59, 136, 140, 141, 142; 502/118, 120; 987/2, 3

[56] References Cited

U.S. PATENT DOCUMENTS 5,624,711  4/1997  Sundberg et al. .............. 427/261

OTHER PUBLICATIONS

Chenera et al. (1995), "Protodetachable arylsilane polymer linkages for use in solid phase organic synthesis," J. Am. Chem. Soc. 117:11999–12000.

Donaldson (1997), "Preparation and reactivity of acyclic (pentadienyl)iron(1+) cations: applications to organic synthesis," Aldrichimica Acta 30(1):17–24.

Farrall et al. (1976), "Bromination and lithiation: two important steps in the functionalization of polystyrene resins," J. Org. Chem. 41(24):3877–3882.

Gordeev et al (1996), "Approaches to combinatorial synthesis of heterocycles: a solid–phase synthesis of 1,4-dihydropyridines," J. Org Chem. 61:924–928.

Han et al. (1996), "Silicon directed ipso-substitution of polymer bound arylsilanes: preparation of biaryls via the suzuki cross–coupling reaction," Tetrahedron Letters 37(16): 2703–2706.

Holmes et al. (1995), "Reagents for combinatorial organic synthesis: development of a new o-nitrobenzyl photolabile linker for solid phase synthesis," J. Org. Chem. 60:2318–2319.

Murphy et al. (1995), "Combinatorial organic synthesis of highly functionalized pyrrolidines: identification of a potent angiotensis converting enzyme inhibitor from a mercaptoacyl proline library," J. Am. Chem. Soc. 117:7029–7030.

Pearson (1989), "Recent developments in the synthetic applications of organoiron and organomolybdenum chemistry," in Advances in Metal–Organic Chemistry, vol. 1, pp. 1–49.

Plunkett et al. (1995), "A silicon-based linker for traceless solid–phase synthesis," J. Org. Chem. 60:6006–6007.

Ruhland et al. (1996), "Solid–supported combinatorial synthesis of structurally diverse β-lactams," J. Am. Chem. Soc. 118:253–254.

Toda et al. (1996), "1:1 and 2:1 inclusion complexes of (R,R)-(-)-trans-2,3-bis(hydroxydiphenyl-methy)-1,4-dioxaspiro[4,4]nonane with N-allylfuran-2-carboxanilide which upon irradiation in the solid state give (-) and (+)-photocyclization products, respectively," J. Org. Chem. 61:6490–6491.

*Primary Examiner*—Porfirio Nazario-Gonzalez
*Attorney, Agent, or Firm*—William B. Kezer; Lauren L. Stevens

[57] ABSTRACT

Compositions and methods for the solid phase synthesis of organic compounds are provided. The compositions are solid supports having an attached traceless linker precursor and are represented by the formula:

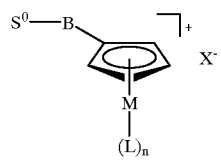

In this formula, $S^0$ is a solid support; B is a connecting group; M is a transition metal, for example ruthenium, chromium, iron, molybdenum and manganese; each L is independently a transition metal ligand; the letter n represents an integer of from 1 to 4, such that M has a sufficient number of ligands to fill the available valences; and $X^-$ represents an anion which is typically a non-nucleophilic anion.

15 Claims, 7 Drawing Sheets

Iron Dicarbonyl Phosphine (or Phosphite) Complexes of Dienes

Fig. 3b

Immobilized Cyclopentadienyl Molybdenum Dicarbonyl Diene Complexes

ARENE-TRANSITION METAL LINKERS FOR SOLID PHASE SYNTHESIS

BACKGROUND OF THE INVENTION

Current drug discovery programs are increasingly incorporating solution and solid-phase combinatorial chemistry processes to provide large libraries of potentially active compounds. See, for example, Choong, et al., "Solid-Phase Synthesis: Applications to Combinatorial Libraries" in ANNUAL REPORTS IN MEDICINAL CHEMISTRY, Bristol, ed., Academic Press, San Diego, Calif., Volume 31, pp. 309–318 (1996).

A prerequisite for any solid-phase organic synthesis is a method for immobilizing a first building block to a polymeric support. The most commonly used approaches tether a bifunctional building block (e.g., an amino acid) via acylation to an amino- or hydroxy- moiety at the terminus of a cleavable linker. Upon completion of the compound synthesis, the product is cleaved from the support. The product typically carries with it some polar functional group residue (e.g., a carboxamide or carboxylic acid) as a vestige of its site of attachment to the resin. The application of this strategy to the preparation of a combinatorial library of compounds results in each of the compounds having a common functional group (or linker residue). This common functional group in each of the library members can represent a liability as it can potentially impart an undesired common physico-chemical characteristic on an otherwise diverse set of structures.

One approach to the problem of linker residues present in combinatorial libraries is the development of aryl-silane linker groups. These groups can be cleaved from a solid support by strong acid or fluoride ion via ipso hydrodesilation. See, for example, Plunkett, et al., *J. Org. Chem.* 60:6006 (1995); Chenera, et al., *J. Am. Chem. Soc.* 117:11999 (1995); Han, et al., *Tetrahedron Lett.* 37:2703 (1996); and Boehm, et al., *J. Org. Chem.* 61:6490 (1996). These aryl-silane linker groups have been termed "traceless" linkers since the liberated products contain no obvious signature of the site of their attachment to the solid support. One limitation to existing methods for employing such linkers in construction combinatorial libraries is that a specialized, multi-step synthesis is required for each aromatic building block that is to be tethered to a solid support. Additionally, the use of strong acid or fluoride ion to cleave such linkers is not compatible with a large number of pharmacophore functional groups typically found in combinatorial libraries.

What is needed in the art are new traceless linkers which allow the tethered products to be released using mild procedures such as photolysis. The present invention provides such linkers, methods for their preparation and methods for their use.

SUMMARY OF THE INVENTION

The present invention provides compositions and methods for the solid phase synthesis of organic compounds. The compositions are solid supports having an attached traceless linker precursor and are represented by the formula:

In this formula, $S^0$ is a solid support; B is a connecting group; M is a transition metal, for example ruthenium, chromium, iron, molybdenum and manganese; each L is independently a transition metal ligand; the letter n represents an integer of from 1 to 4, such that M has a sufficient number of ligands to fill the available valences; and $X^-$ represents an anion which is typically a non-nucleophilic anion.

In another aspect, the present invention provides compositions comprising an arene-containing compound on a solid support. These compositions are represented by the formula:

The symbols $S^0$, B, M and $X^-$ have the same meanings provided above. The symbol Ar represents an arene-containing compound attached to M through an $\eta^6$-arene π-complex.

In still another aspect, the present invention provides methods of preparing a substituted arene compound on a solid support. According to these methods, a scaffold for synthesis is selected or prepared which comprises a solid support having an attached precursor arene moiety. The scaffold has the formula:

wherein each of $S^0$, B, M and $X^-$ have the meanings provided above; each R is independently a substituent on the arene portion of the scaffold; and m is an integer of from 1 to 6. The precursor arene compound is then converted to a target arene compound using any synthetic methods which are compatible with the solid support, transition metal complex and other functionalities present in the precursor arene compound.

In yet another aspect, the present invention provides a library of arene-containing compounds on a solid support, each member of the library independently having the formula:

Each of the symbols S⁰, B, M, Ar and X⁻ has the meaning provided above.

BRIEF DESCRIPTION OF THE DRAWINGS

FIG. 3 illustrates additional uses of traceless linkers employed phosphine ligands (3a) and molybdenum diene complexes (3b).

DETAILED DESCRIPTION OF THE INVENTION

Definitions

As used herein, the term "alkyl" refers to a saturated hydrocarbon radical which may be straight-chain or branched-chain (for example, ethyl, isopropyl, τ-amyl, or 2,5-dimethylhexyl) or cyclic (for example cyclobutyl, cyclopropyl or cyclopentyl). The term "alkylene" refers to an alkyl linking group or diradical (e.g., a methylene, ethylene or propylene linking group).

The term "alkoxy" refers to an alkyl radical as described above which also bears an oxygen substituent which is capable of covalent attachment to another hydrocarbon radical (such as, for example, methoxy, ethoxy and τ-butoxy).

The term "arene" or "arene compound" refers to a compound having at least one aromatic substituent which may be a single ring or multiple rings which are fused together, linked covalently or linked to a common group such as an ethylene or methylene moiety. The aromatic rings may each contain heteroatoms, for example, phenyl, naphthyl, biphenyl, diphenylmethyl, 2,2-diphenyl-1-ethyl, thienyl, pyridyl and quinoxalyl. The aromatic rings may also be optionally substituted with halogen atoms, or other groups such as nitro, carboxyl, alkoxy, phenoxy and the like. Additionally, the aryl radicals may be attached to other moieties at any position on the aromatic ring which would otherwise be occupied by a hydrogen atom (such as, for example, 2-pyridyl, 3-pyridyl and 4-pyridyl). For the present invention, "arene compounds" are those compounds which are capable of forming $\eta^6$-arene π-complexes with a transition metal ion.

The term "protecting group" as used herein, refers to any of the groups which are designed to block one reactive site in a molecule while a chemical reaction is carried out at another reactive site. More particularly, the protecting groups used herein can be any of those groups described in Greene, et al., *Protective Groups In Organic Chemistry*, 2nd Ed., John Wiley & Sons, New York, N.Y., 1991, incorporated herein by reference. The proper selection of protecting groups for a particular synthesis will be governed by the overall methods employed in the synthesis. Protecting groups are typically removed by chemical methods and include groups such as Fmoc, Dmt and others known to those of skill in the art.

General—Traceless Linkers

The present invention is the result of the surprising discovery that transition metal complexes can be used as traceless linkers for the preparation of a wide variety of compounds on a solid support. In brief, the underlying premise is that a transition metal can be complexed with an electron-donating species which is attached to a solid support and further complexed with an arene compound to form support-bound organometallic "sandwich" complexes. These complexes are similar in structure to metallocene complexes (e.g., ferrocene). Particularly surprising was the discovery that certain complexes are suitable for multiple synthetic applications as the attached arene groups can be removed from the support while leaving tie support-bound transition metal in place.

In general, the compositions will comprise a solid support having at least one attached electron-donating group which is complexed to a transition metal as depicted below.

According to this formula, the symbol S⁰ represents a solid support, the letter B represents a linkage or a bond, ED is an electron-donating group, M is dle transition metal, L is a metal ligand, n is an integer to satisfy the available valences on the metal and X⁻ is a suitable counterion.

The symbols S⁰, B, M, L, n and X⁻ are discussed in detail below with regard to preferred embodiments in which ED is a cyclopentadienyl group. However, the present invention is not so limited and the metal can be attached through a variety of electron-donating ligands, including π-allyl groups, cyclooctadienyl groups, cyclopentadienyl groups, indenyl groups, fluorenyl groups, azulene groups, phosphines, phosphites and tris(pyrazoyl)borate groups (see, for example, Lukehart, FUNDAMENTAL TRANSITION METAL ORGANOMETALLIC CHEMISTRY, Brooks-Cole, Monterey, Calif., (1985) pp. 85–118, incorporated herein by reference). These groups indicate the diversity of the present invention. In particular, from the above ED examples, one of skill in the art will understand that the transition metal can be covalently attached to the support through a π-allyl complex, an $\eta^6$ complex, or a monoanionic ligand which acts as a six-electron donor (like the $\eta^6$ complexes). In other embodiments, the metal can be attached to the solid support through an electron donating group such as a phosphine or phosphite.

Thus, the compositions for solid phase synthesis of arene compounds described herein are solid supports which have been modified with a traceless linker. The traceless linker comprises a transition metal which is linked to the solid support via complex formation as described above. The particular complex selected for attachment of the transition metal to the solid support should be rigorous enough to withstand any subsequent reaction conditions and should further withstand any conditions necessary for the removal of a the modified arene compound from the metal.

Figure 1:
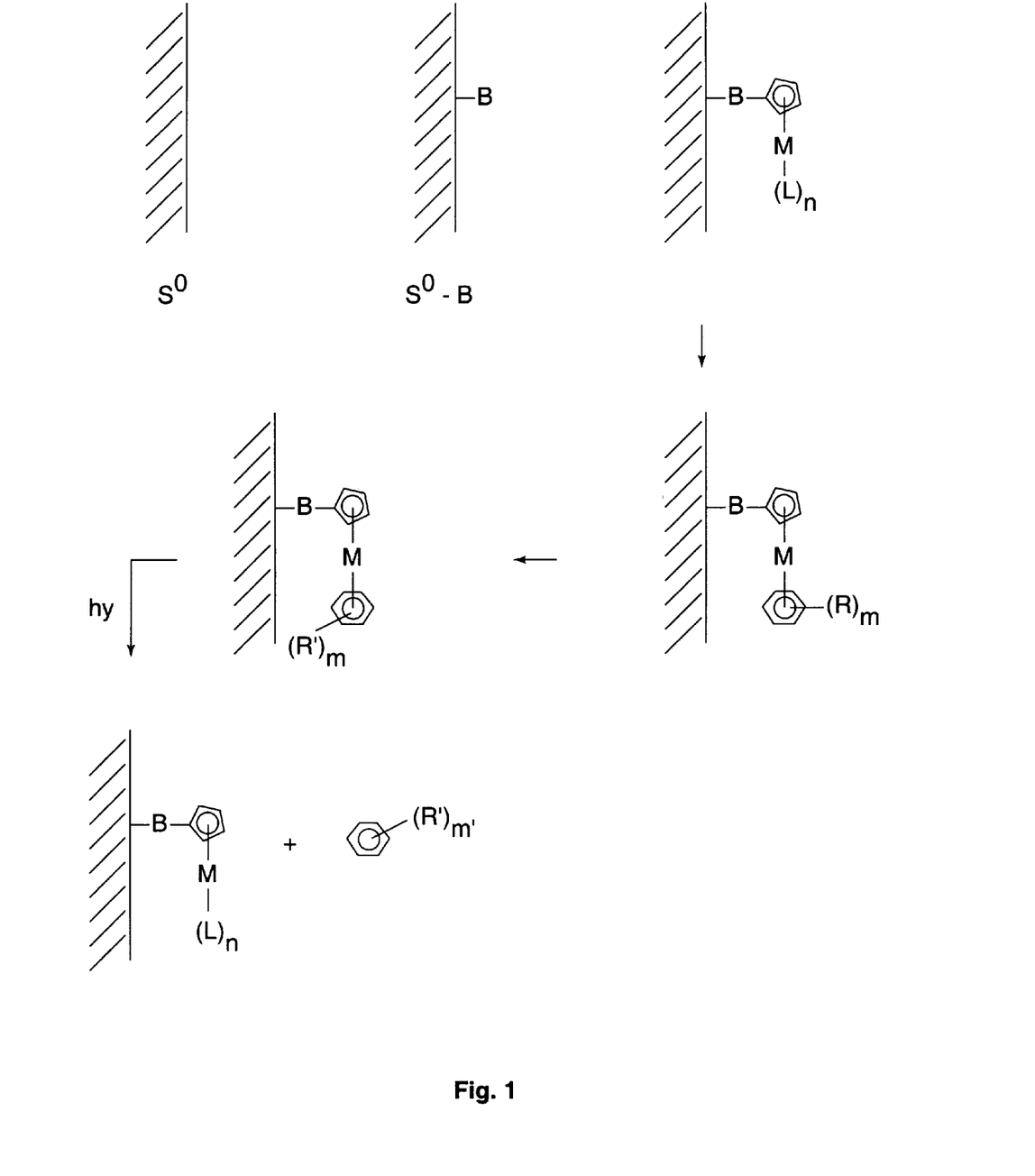
FIG. 1 shows one approach to the solid phase synthesis of compounds of the present invention, whether individually or as a member of a library.

Illustrated in FIG. 1 is a general strategy for the use of these new linkers in the solid phase synthesis of substituted arenes. As can be seen in this figure, a suitable transition metal complex (depicted as a cyclopentadienyl complex for clarity) is attached to a solid support, via a connecting group (represented by B). The attached organometallic complex includes a metal atom having exchangeable ligands (L). Upon treatment of the attached organometallic complex with an arene compound, the ligands are displaced and the arene compound is attached to the metal atom via an $\eta^6$-arene π-complex. Modifications to the attached arene compound (depicted as the conversion of $(R)_m$ to $(R')_m$ can then be carried out using synthetic methods which are compatible with the solid support and traceless linker. Removal of the modified arene compound (or target arene compound) from the organometallic complex can be accomplished under photolytic or thermolytic conditions.

Figure 2:
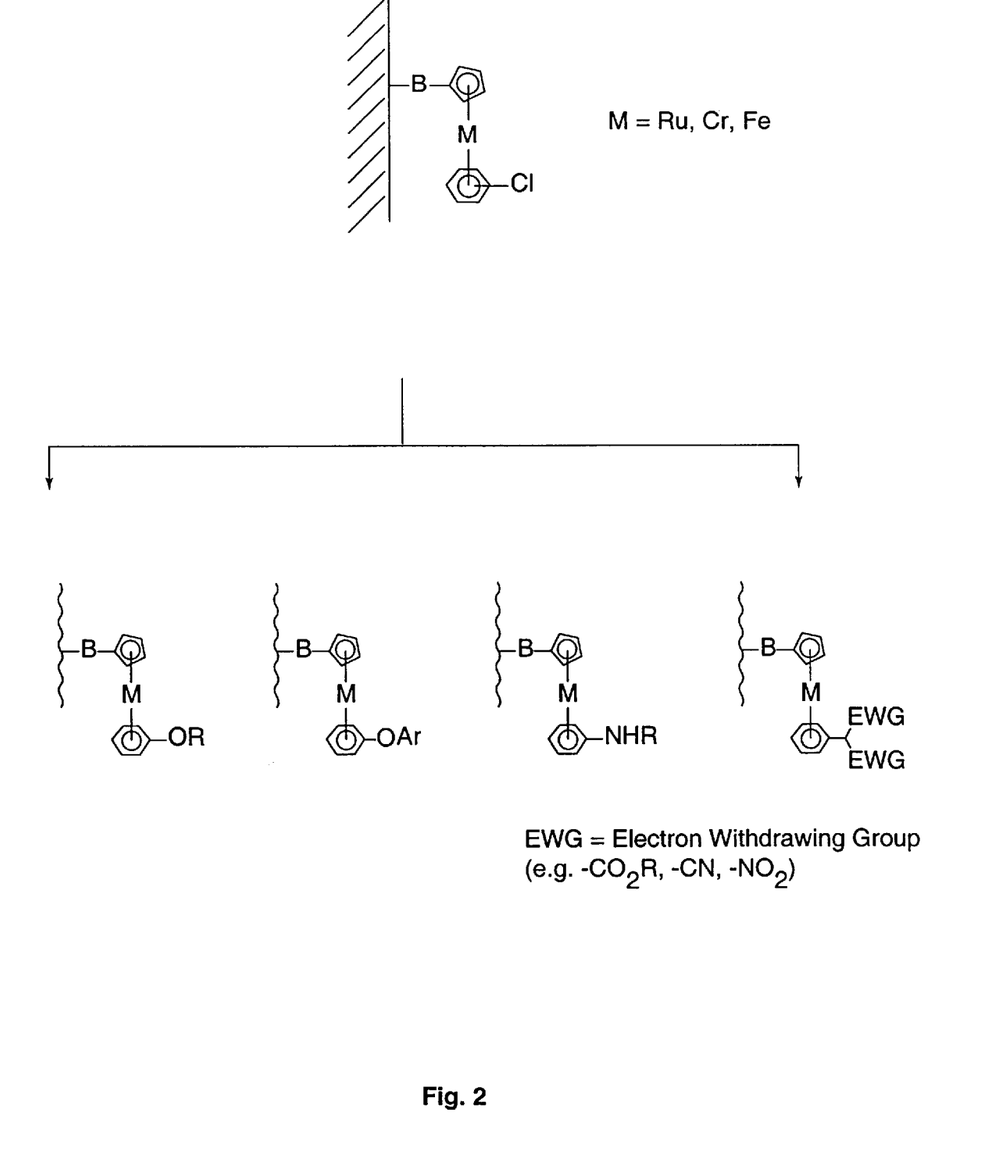
FIG. 2 illustrates the use of a traceless linker for the preparation of a substituted arene compound in which modifications are made to the arene ring via aromatic substitution reactions.

In addition to providing modified arenes having no residual functionality from the linkers, the present methods provide additional benefits. For example, the aromatic ring which is complexed to the metal atom is activated towards nucleophilic aromatic substitution reactions. Suitable nucleophiles useful in these aromatic substitution reactions include alkoxides, phenolates, mercaptides, amines and stabilized carbanions. Each of these groups have been found to displace chloride from ruthenium-bound chlorobenzenes (see FIG. 2). Other haloaromatic groups (e.g., 4- or 5-chloroindoles) react similarly when coordinated as π-complexes to cationic metal centers such as ruthenium. This feature expands the types of modified arene compounds which can be prepared beyond those which are available using conventional, non-activating linkers.

Figure 3A:
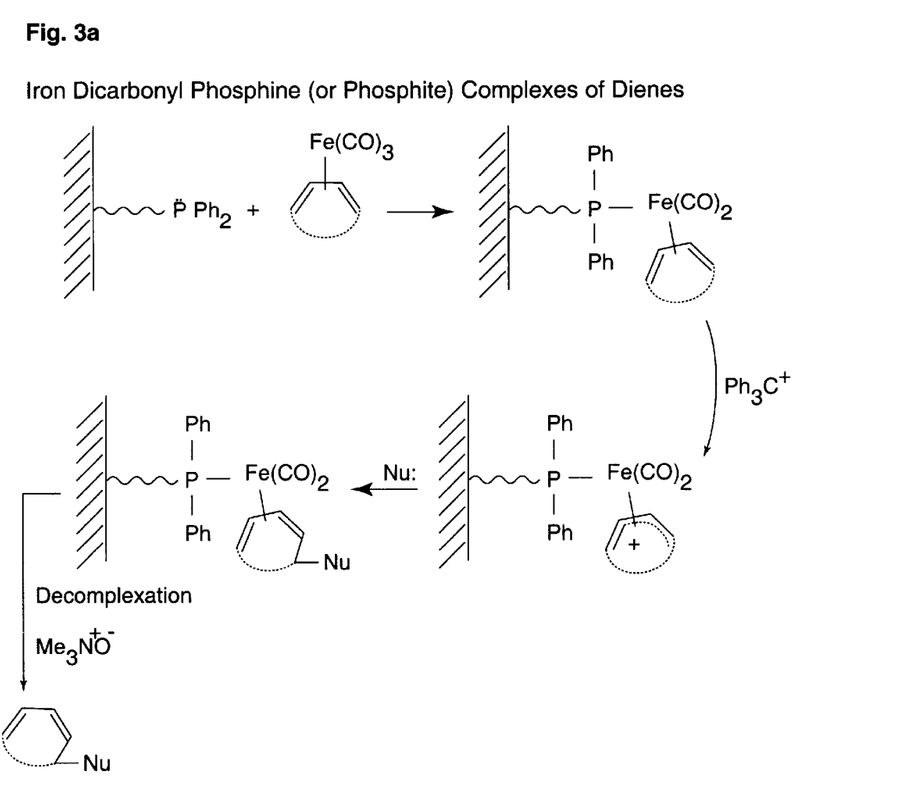

FIGS. 3a and 3b provide an illustration of the additional scope of the present invention. In particular, FIG. 3a illustrates the attachment of a metal-diene complex to a resin-bound phosphine ligand. One of skill in the art will understand that for certain metals, resin-bound phosphite ligands can also be used. Following the attachment of the metal-diene complex to the solid support, chemistry can be carried out on the diene portion and the modified diene can be de-complexed as shown. The types of chemistry available are limited only by considerations of compatibility with the support and the robust nature of the metal-diene complex.

Figure 3B:
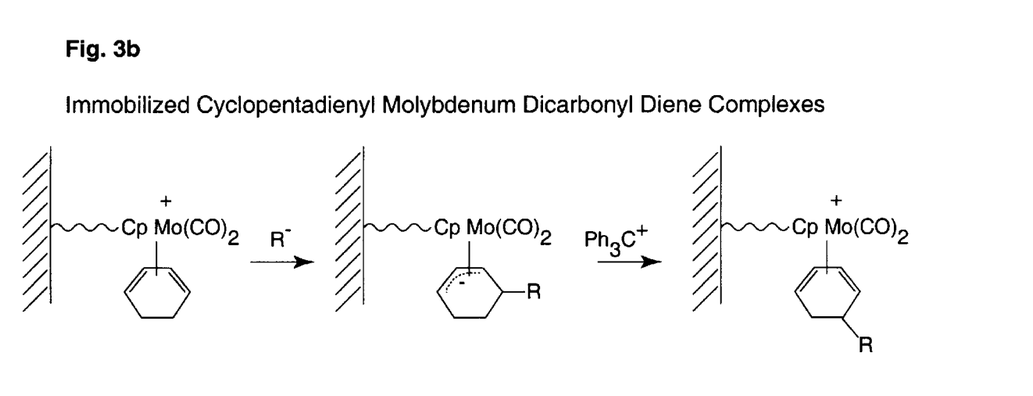

FIG. 3b illustrates the use of an immobilized cyclopentadienyl molybdenum dicarbonyl diene complex. This embodiment indicates the diversity of chemistry which can be achieved with support-bound metal diene complexes (in addition to the arene chemistry discussed both above, and in more detail below). According to scheme provided in FIG. 3b, a molybdenum dicarbonyl diene complex is attached to a support-bound cyclopentadienyl moiety (as described herein) and treated with an anionic species ($R^-$, for example methyllithium or phenyl magnesiumbromide). Further treatment with, for example, trityl cation and decomplexation provides a diene modified with R. Additional examples and conditions for metal-diene complex reactions can be found in Pearson, ADVANCES IN METAL-ORGANIC CHEMISTRY, Vol. 1, JAI Press Inc., pp. 1–49 (1989) and in Donaldson, Aldrichimica Acta 30(1):17–24 (1997), the disclosures of each being incorporated herein by reference.

Support-Bound Traceless Linkers

In view of the above, the present invention provides in one aspect solid supports which have been modified to have an attached traceless linker. These modified solid supports are represented by the formula:

In this formula, the symbol $S^0$ represents the solid support; B represents a connecting group; M represents a transition metal; and each L independently represents a ligand to the transition metal M, which occupies the remaining available valences on the metal. Accordingly, the lowercase letter n represents an integer of from 1 to 4 which will be dependent on the particular metal used and will be selected to provide M with a sufficient number of ligands to occupy the available valences. The symbol $X^-$ represents an anionic group, typically a non-nucleophilic anionic group.

In this aspect of the invention, the solid supports or substrates may be biological, nonbiological, organic, inorganic, or a combination of any of these, existing as particles, strands, precipitates, gels, sheets, tubing, spheres, containers, capillaries, pads, slices, films, plates, etc. The solid support is preferably a spherical bead, but may take on alternative surface configurations. For example, the solid support can be a flat surface and can contain raised or depressed regions on which synthesis takes place. Suitable supports include, for example, the support may be a polymerized Langmuir Blodgett film, functionalized glass, Si, Ge, GaAs, GaP, $SiO_2$, $SiN_4$, modified silicon, or any one of a variety of gels or polymers such as polystyrene, (poly) tetrafluoroethylene, (poly)vinylidendifluoride, polycarbonate, or combinations thereof. Other suitable solid support materials will be readily apparent to those of skill in the art. Preferably, the surface of the solid support will contain reactive groups, which are carboxyl, amino, hydroxyl, thiol, or the like. More preferably, the surface will have surface Si—OH functionalities, such as are found on silica surfaces.

Attached to the surface of the solid support is a connecting group, B. In one group of embodiments, B will be attached to the solid support via carbon-carbon bonds using, for example, substrates having (poly)trifluorochloroethylene surfaces, or more preferably, by siloxane bonds (using, for example, glass beads or silicon oxide as the solid support). Siloxane bonds with the surface of the support are formed in one embodiment via reactions of derivatization reagents bearing trichlorosilyl or trialkoxysilyl groups. The particular connecting group can be selected based upon its hydrophilic or hydrophobic properties to improve presentation of an attached transition metal component to subsequent synthesis reagents. Prior to attachment to the solid support the connecting group will have a substrate attaching group at one end. For example, substrate attaching groups appropriate for attachment to a silica surface would include trichlorosilyl and trialkoxysilyl functional groups.

In one group of embodiments, B is a connecting group having the formula:

in which $R^1$ and $R^2$ are each independently a lower alkyl or lower alkoxy group and Y is a divalent radical which is an alkylene radical optionally interrupted by one or more —O—, —S—, —CO—, —CONH—, —CSNH—, —CO$_2$—, —CONR—, —CSNR—, —OCONH—, or —OCONR— linkages, or combinations thereof, in which R is an alkyl group having from 1 to 8 carbon atoms. For example, Y can be an alkylene radical having from 1 to 24 carbon atoms (e.g., —CH$_2$CH$_2$CH$_2$—, —CH$_2$CH$_2$CH$_2$CH$_2$CH$_2$— or —(CH$_2$)$_2$—). Alternatively, Y can be, for example, —CH$_2$OCH$_2$—, —CH$_2$CH$_2$CONHCH$_2$CH$_2$—, —CH$_2$COCH$_2$—, —CH$_2$CH$_2$CONRCH$_2$—, and the like.

In other embodiments, B can be a polyethyleneglycol, polyethyleneimine, polyacrylamide, polyvinylalcohol, polystyrene and combinations thereof.

The use of solid supports or connecting groups which contain aromatic rings (e.g., polystyrene supports or phenyl-containing spacers) present certain synthetic challenges in order to prevent η$^6$-complexes from forming with groups other than the arene compound to be modified. Accordingly, the use of polystyrene as either the support or connecting group will typically involve additional manipulations such as, for example, the control of functional site density on the surface of the support, described in co-pending application Ser. No. 08/431,196, now U.S. Pat. No. 5,624,711, incorporated herein by reference, or additional cross-linking to provide a more rigid polystyrene support which is less reactive with a transition metal. Preferably, the use of spacers or connecting groups having aromatic rings will employ the techniques of controlling functional site density. For example, a solid support can be modified by affixing functional sites (in this embodiment, connectors having aromatic rings) to the surface of a solid substrate at a preselected density. The solid substrate is contacted with a mixture of connecting groups and diluent molecules. The connecting groups each have reactive groups which are capable of covalent attachment to the support and a functional group which is optionally protected. The diluent molecules have only a single reactive site which reacts with the surface of the support. The ratio of the connecting molecules to the diluent molecules in the mixture is selected to control the resultant functional site density on the surface of the support. The contact is carried out for a sufficient period of time to bind the connecting groups and the diluent molecules to the support.

Attached to the connecting group, B, is a cyclopentadienyl moiety which is complexed to a transition metal atom, M. The nature of the complex between the cyclopentadienyl moiety and the transition metal atom is a η$^5$-cyclopentadienide π-complex (depicted in the formulae herein as a single bond to the center of the cyclopentadienide moiety). A number of transition metals will form such complexes including, for example, Fe, Co, Ni, Cr, Ti, V, and Ru. See, Lukehart, FUNDAMENTAL TRANSITION METAL ORGANOMETALLIC CHEMISTRY, Brooks-Cole, Monterey, Calif., (1985) pp. 85–118, incorporated herein by reference. In preferred embodiments, the metal is Ru, Mn, Mo or Fe, more preferably Ru.

Figure 4:
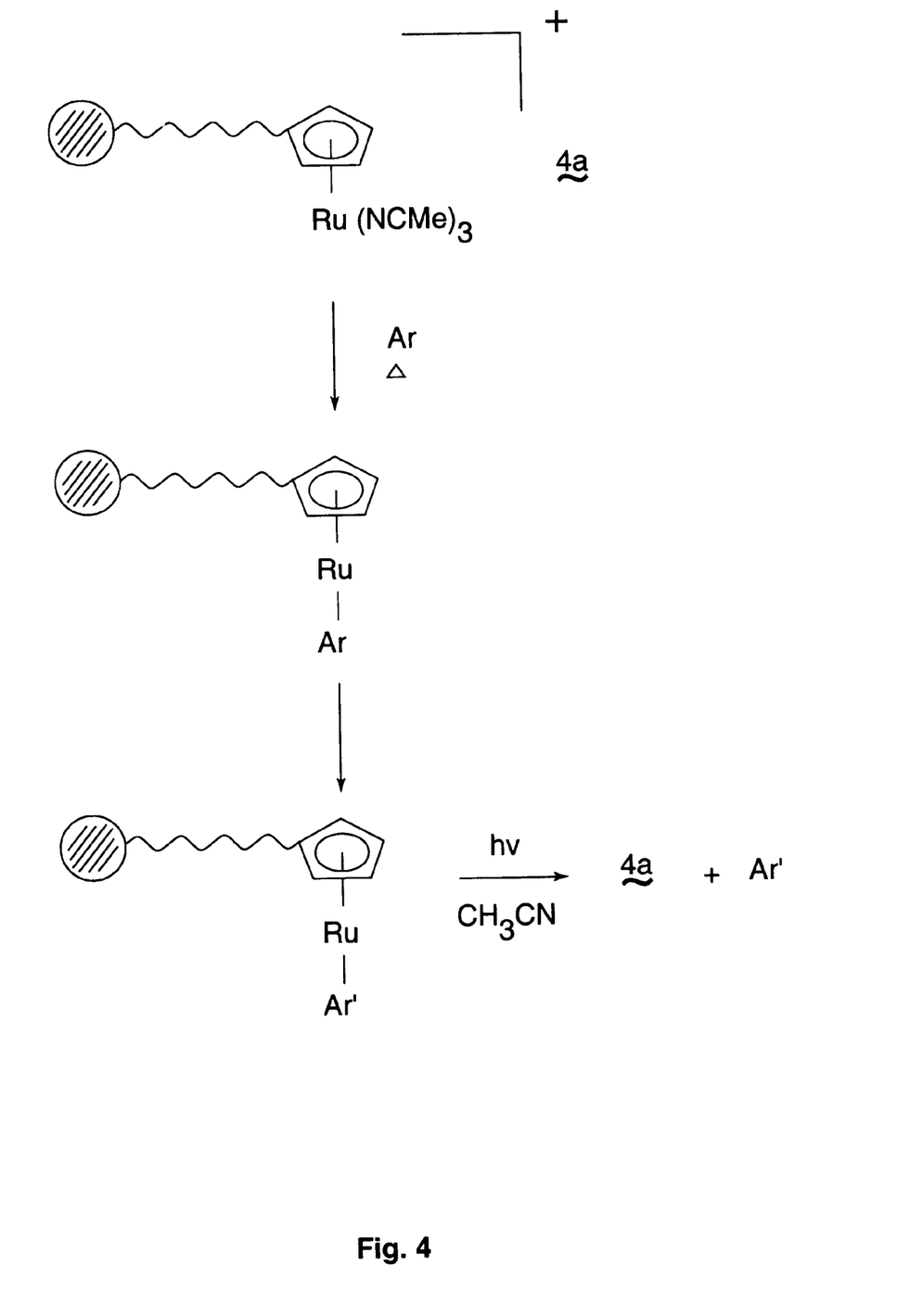
FIG. 4 illustrates the use of traceless linkers in a reversible manner to regenerate the starting modified solid support.

Depending on the particular metal atom used, a number of valences will be occupied by additional ligands (L in the above formula). A variety of ligands are suitable for use in this aspect of the invention. However, preferred ligands are those which can be readily displaced to allow the metal atom to form an η$^6$-arene π-complex upon exposure to a suitable arene compound. Still further preferred are those ligands which render the traceless linker "reversible." FIG. 4 illustrates the use of ligands which provide a reversible modified support. In this figure, the solid support is represented by a shaded sphere and the connecting group is a wavy line attached to the cyclopentadienyl moiety. Complexed to the cyclopentadienide moiety is a ruthenium atom having three acetonitrile groups as ligands (4a). Arenes (Ar) are captured by this immobilized complex (4a) upon thermolysis at 50–100° C. in dichloroethane solution. Following modifications to the arene (to provide Ar'), release of the modified arene is accomplished by photolysis in acetonitrile. Under these conditions, the immobilized complex (4a) is regenerated for subsequent use. Other examples of suitable ligands include neutral electron-donating ligands such as simple nitriles, carbon monoxide and ethylene or other simple olefins. Still other suitable ligands include arenes or aromatic rings.

Each of the attached traceless linkers is positively charged and therefore has an associated counterion, X$^-$. A variety of counterions are suitable for use in the present invention and can be selected depending on subsequent chemistry to be carried out on the support. For example, X$^-$ can be Cl$^-$, PF$_6^-$, SbF$_6^-$, BF$_4^-$ and the like. In preferred embodiments, the counterion is a non-nucleophilic counterion selected from PF$_6^-$, SbF$_6^-$ and BF$_4^-$. Other counterions are known to those of skill in the art.

Figure 5A:
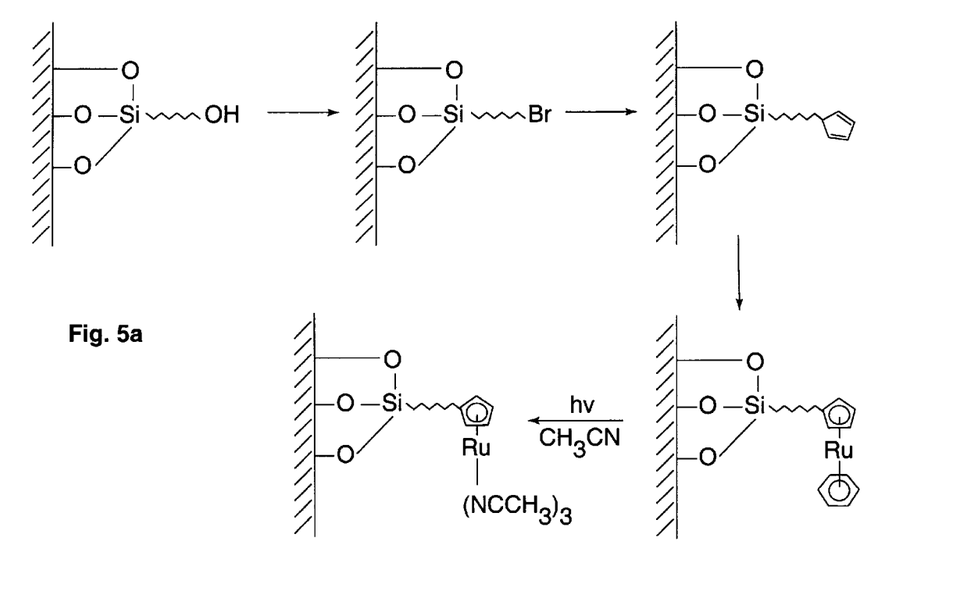
FIG. 5 illustrates several synthetic methods which are useful for the preparation of solid supports having traceless linkers.

Preparation of complexes of formula I can be carried out using standard synthetic methods. For example, FIG. 5a illustrates one method of attaching a transition metal-arene traceless linker to a solid support. In this figure, a glass bead (or CPG) is treated with a hydroxyalkylsilane to provide a derivatized solid support having attached hydroxyalkyl groups. Conversion of the hydroxyalkyl group to a bromoalkyl or a chloroalkyl group can be accomplished using standard methods (e.g., PBr$_3$, Ph$_2$PBr$_3$, POCl$_3$, PCl$_5$). Displacement of the bromide with cyclopentadienide ion provides a tethered cyclopentadienyl group. Treatment of the tethered cyclopentadienyl group with a suitable base (e.g., methyllithium in THF) followed by [(η$^6$-C$_6$H$_6$)RuCl$_2$]$_2$ (available from Aldrich Chemical Company, Milwaukee, Wisc., USA) provides a tethered transition metal traceless linker. Replacement of the remaining benzene ring with acetonitrile ligands can be accomplished by irradiation of the complex in the presence of acetonitrile.

Figure 5B:
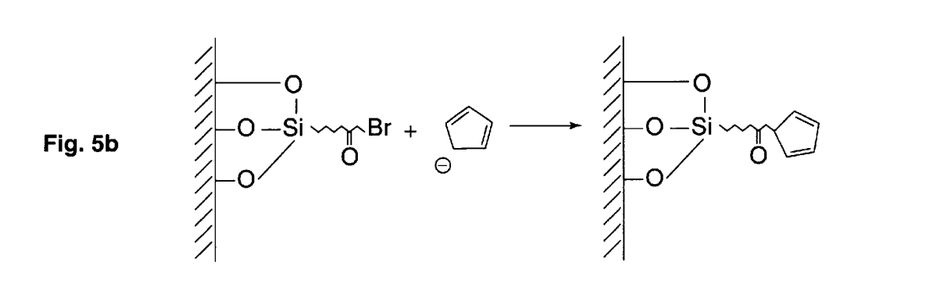
Figure 5C:
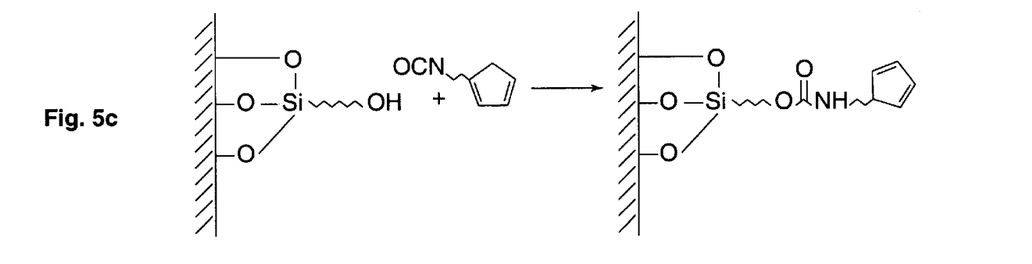

Alternative chemistries can also be employed to attach a cyclopentadienyl group to a derivatized solid support. A variety of these methods are based on the nucleophilic reactivity of the cyclopentadienide anion. For example, displacement of a halide from an α-halomethylketone which is attached to a solid support can be accomplished (see FIG. 5b) to provide a tethered cyclopentadienylmethylketone. Still 20 further, a cyclopentadiene can be reacted with suitable components to introduce functionality onto the cyclopentadiene ring which can later be attached to a support or derivatized support (see FIG. 5c).

Figure 6A:
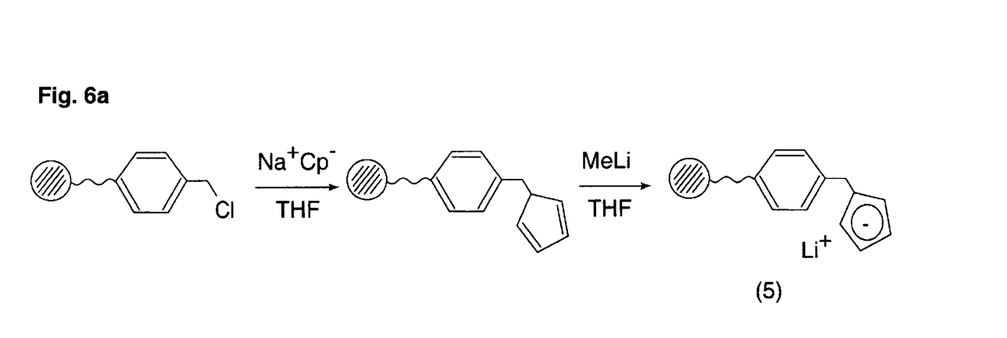
FIG. 6 illustrates the use of polystyrene resin in the preparation of solid supports having traceless linkers.
Figure 6B:
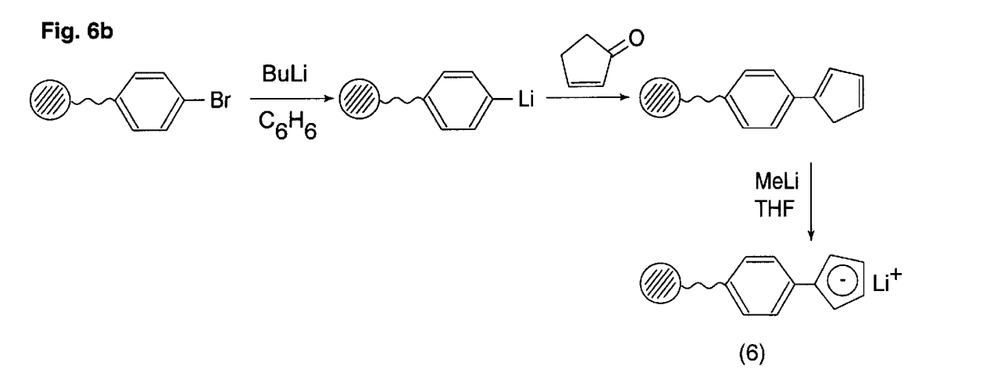
Figure 6C:
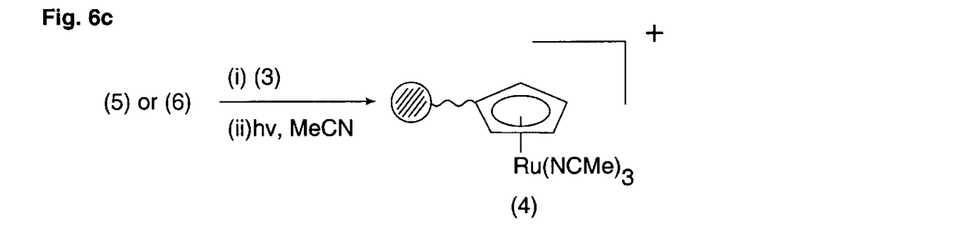

In still other embodiments a chloromethyl polystyrene resin is useful as the support and connecting group. In these embodiments, chloride displacement from the resin can be accomplished with sodium cyclopentadienide. Subsequent lithiation furnishes the resin depicted in FIG. 6a. Alternatively, unfunctionalized polystyrene can be lithiated (see, Farrell, et al., J. Org. Chem. 41:3877 (1976)), and the anion quenched with cyclopentenone and then lithiated as before to provide the polymer-supported cyclopentadienide (see FIG. 6b). Reaction of either of the resins in FIG. 6a or FIG. 6b with a suitable ruthenium complex and subsequent photolysis in acetonitrile delivers the desired resin bearing a traceless linker (see 6c).

Support-Bound Arene-Metal π-Complexes

Figure 7:
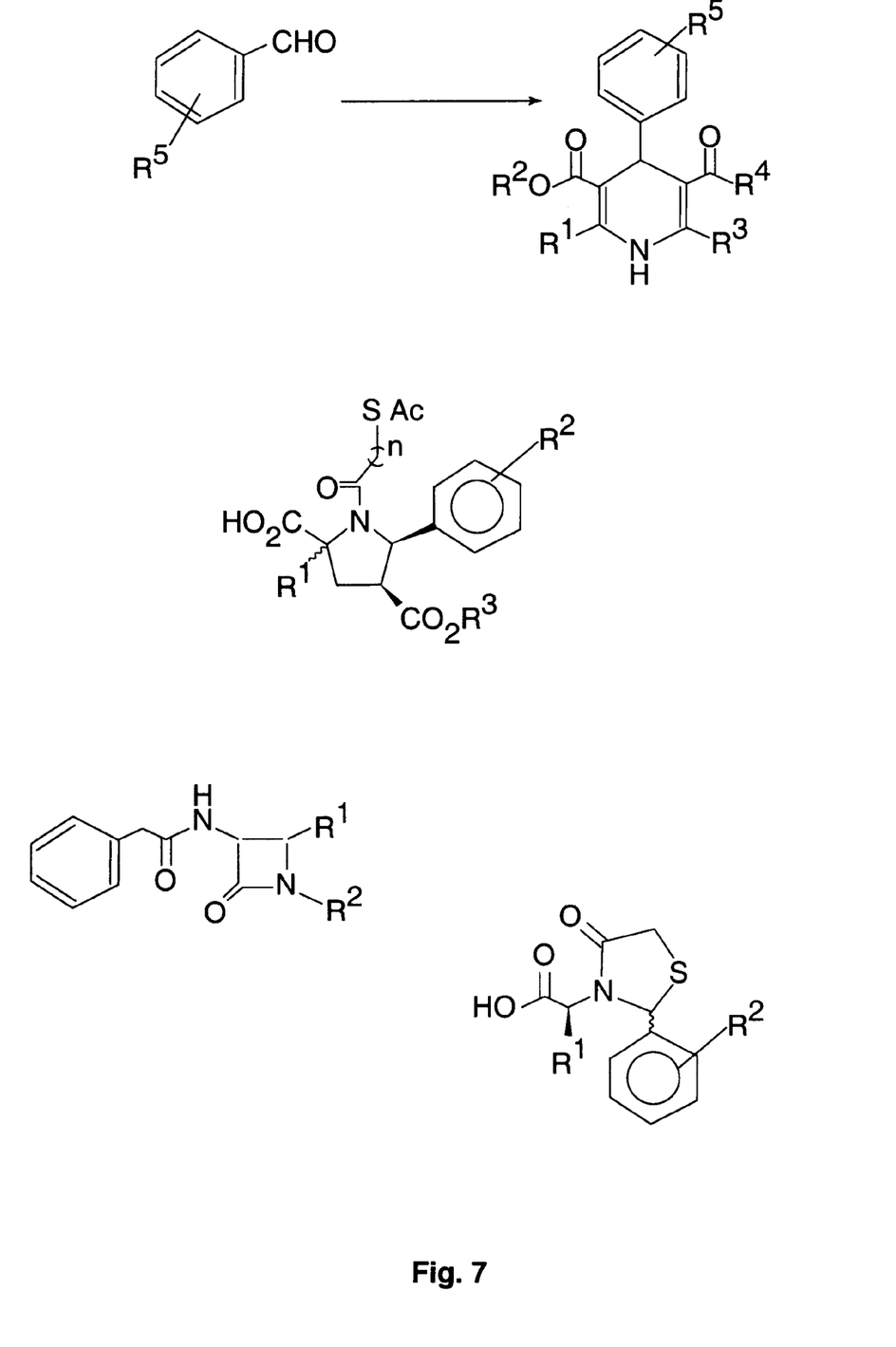
FIG. 7 illustrates a number of arene compound templates which are useful in the present invention.

In another aspect, the present invention provides an arene compound on a solid support. These compositions have the formula:

in which $S^0$, B and M are as defined above, and Ar is an arene compound attached to M through an $\eta^6$-arene π-complex. As used herein, the term "arene compound" refers to those compounds containing an aromatic ring which is capable of forming an $\eta^6$-arene π-complex. The arene-containing compound can be a single ring structure or multiple rings either fused together or linked covalently. Additionally, the arene compound can be a single aromatic ring which is linked to a large organic compound such as a peptide or other biologically active compound. Examples which illustrate the diversity of "arene compounds" are provided in FIG. 7. This definition for an arene compound applies to both precursor arene compounds and target arene compounds (discussed in more detail below). In one group, the arene compound is a substituted benzaldehyde which can be used to construct 4-phenyl-1,4-dihydropyridines. Additional diversity on this template can be introduced at four different positions. Alternative target structures are the N-acyl pyrrolidines which have recently been prepared on a solid support via an azomethine ylide cycloaddition. See Murphy, et al., *J. Am. Chem. Soc.* 117:7029 (1995). By using the aromatic ring for attachment to a transition metal traceless linker, additional functionality and diversity can be introduced in place of the carboxylic acid. β-lactam antibiotics can be prepared on a solid support with a traceless linker by attaching the aromatic ring of a phenylacetyl group to a transition metal and proceeding with synthesis using solid-phase methods as outlined in Ruhland, et al., *J. Am. Chem. Soc.* 118:253 (1996). Still other compounds which can be prepared include the 4-thiazolidinones described in Holmes, et al., *J. Org. Chem.* 60:7328 (1995). Here, preparation begins by attaching a suitable aromatic aldehyde to a transition metal traceless linker.

In other embodiments, the arene compound is an aromatic amino acid, for example, phenylalanine, phenylglycine, tyrosine, tryptophan or the like. As used herein the term amino acid is meant to include both naturally-occurring amino acids (of D- and L-forms) and synthetic, or non-natural amino acids (e.g., phenylglycine). The use of an aromatic amino acid in the compositions and methods of the present invention provides a novel route into the preparation of peptides and proteins in which chain extension can be carried out on either terminus of the amino acid or peptide.

Methods of Preparing a Substituted Arene Compound on a Solid Support

The modified supports described above are useful in the preparation of substituted arenes. As used herein and throughout the specification, the terms "arene," "substituted arene" and "arene compound" refers to any compound having an aromatic ring which is capable of forming a $\eta^6$-arene π-complex with a transition metal. Examples of "arenes" range from simple monohalo-substituted benzenes to organic molecules such as vancomycin which contain aromatic rings as substituents to even larger molecules having at least one aromatic ring.

In general, the methods include:
(a) selecting a scaffold for synthesis comprising a solid support having an attached precursor arene compound; and (b) converting the precursor arene compound to a target arene compound.

In preferred embodiments, the methods will also include an additional step
(c) removing the target arene compound from the solid support.

The scaffold which is used in the present methods will have the formula:

in which $S^0$, B, M and $X^-$ are as described above. The remaining component on the scaffold is an aromatic ring which forms a $\eta^6$-arene π-complex with the metal. Each R group on the aromatic ring is independently a substituent which can be further manipulated or reacted in subsequent steps or a portion of the precursor arene compound on which chemistry can be conducted (using the aromatic ring as an anchor to the solid support). The number of R groups which can be present on the aromatic ring can vary so long as the groups do not interfere with the ability of the aromatic ring to form a π-complex with the metal atom. Thus, the number of R groups will be from one to six, more preferably from one to three.

Selecting an appropriate scaffold, including a precursor arene compound, will depend in large part upon the anticipated chemical reactions to be carried out on the attached precursor arene compound. The precursor arene compounds can be essentially any commercially available compounds containing an aromatic ring, preferably a phenyl or substituted phenyl ring. Alternatively, the precursor arene compounds can be compounds prepared according to literature methods, upon which subsequent modifications and manipulations will be made.

Thus, in one group of embodiments, the scaffold will be a glass bead and the attached precursor arene compound will be a haloaromatic compound. In this group of embodiments, the precursor arene compound can be converted to a target arene compound by nucleophilic displacement reactions on the aromatic ring (displacing one or more of the halogen atoms on the aromatic ring). Preferred haloaromatic precursor arene compounds include chlorobenzene, bromobenzene and iodobenzene.

In other embodiments, the attached precursor arene compound will be an aromatic aldehyde or substituted aromatic aldehyde. By selecting a scaffold having an attached aromatic aldehyde, target arene compounds including, for example, 4-aryl-1,4-dihydropyridines can be prepared. See, Gordeev, et al., *J. Org. Chem.* 61:924–928 (1996), incorporated herein by reference.

In still other embodiments, the precursor arene compound will be an aromatic amino acid, for example, phenylalanine, phenylglycine, homophenylalanine, homotyrosine, tryptophan, tyrosine, homotryptophan, or protected forms thereof. In this group of embodiments, each of the amino and carboxylic acid moieties is optionally protected with a suitable protecting group. Preparation of the target arene compound can be carried out via amide bond forming reactions to form dipeptides, tripeptides, oligopeptides, polypeptides or proteins. The formation of amide bonds on the support-bound aromatic amino acid can be accomplished either by acylation of the amino group, or by amidation of the carboxylic acid group. Other suitable reactions which can be carried out include carboxylic ester forming reactions, and acylation of the amino terminus using, for example, suitable anhydrides. Still other substituted aromatic amino acids can be prepared using chlorophenylalanine (from Sigma Chemical Co., St. Louis, Mo., USA) as the starting material in nucleophilic displacement reactions.

From the above, it is apparent that this aspect of the invention can be carried out using (1) any compound capable of forming a $\eta^6$-arene $\pi$-complex with the traceless linkers described above, and (2) any transformations (precursor arene compound to target arene compound) which are compatible with the components of the scaffold (e.g., solid support, connecting group, and $\eta^5$-cyclopentadienyl transition metal complex).

Accordingly, the step of converting the precursor arene compound to a target arene compound can be carried out using essentially any transformations which are known to be compatible with solid-phase chemistry. Conditions for carrying out a particular transformation would be well known to one of skill in the art and could be determined from such sources as Fieser and Fieser, REAGENTS FOR ORGANIC SYNTHESIS, John Wiley & Sons, New York and ORGANIC SYNTHESES, Organic Syntheses, Inc., Volumes 1–73. Certain transformations should be avoided when particular connecting groups are used. For example, substitutions on a haloaromatic precursor arene compound should not be carried out with alkoxides when the connecting group contains an ester linkage.

Libraries of Support-Bound Arene-Metal $\pi$-Complexes

In yet another aspect, the present invention provides libraries of arene compounds on a solid support, each member of the library independently having the formula:

in which $S^0$, B, M, Ar and $X^-$ have the meanings provided above. The methods of forming these libraries will typically be carried out using the methods described above for the preparation of solid supports having attached traceless linkers in combination with synthetic methods using combinatorial chemistry protocols.

Preparation of the Libraries

A number of solid-phase techniques can be applied to the preparation of libraries of the present invention. In each of the solid-phase techniques, however, a traceless linker is used. A general description of the preparation is provided with reference to FIG. 1.

As shown in FIG. 1 (illustrating only a single compound synthesis), a traceless linker is attached to a solid support to provide a derivatized solid support having a plurality of available arene attaching sites. To the sites in a derivatized support is attached an arene precursor compound which can be selectively modified to form each member of the library. In one group of embodiments, each chemically distinct member of the library will be synthesized on a separate solid support.

A more thorough discussion of the various solid-phase techniques can be found in the patents and publications provided below.

Libraries on a Single Substrate

Flow Channel or Spotting Methods

Additional methods applicable to library synthesis on a single substrate are described in co-pending applications Ser. No. 07/980,523, filed Nov. 20, 1992, and 07/796,243, filed Nov. 22, 1991, incorporated herein by reference for all purposes. In the methods disclosed in these applications, reagents are delivered to the substrate by either (1) flowing within a channel defined on predefined regions or (2) "spotting" on predefined regions. However, other approaches, as well as combinations of spotting and flowing, may be employed. In each instance, certain activated regions of the solid support are mechanically separated from other regions when the monomer solutions are delivered to the various reaction sites.

Pin-Based Methods

Another method which is useful for the preparation of compounds and libraries of the present invention involves "pin based synthesis." This method is described in U.S. Pat. No. 5,288,514, previously incorporated herein by reference. The method utilizes a substrate having a plurality of pins or other extensions. The pins are each inserted simultaneously into individual reagent containers in a tray. In a common embodiment, an array of 96 pins/containers is utilized.

Libraries on Multiple Substrates

Bead Based Methods

Yet another method which is useful, and preferred, for synthesis of compounds and libraries of the present invention involves "bead based synthesis." A general approach for bead based synthesis is described in co-pending application Ser. Nos. 07/762,522 (filed Sep. 18, 1991); 07/946,239 (filed Sep. 16, 1992); 08/146,886 (filed Nov. 2, 1993); 07/876,792 (filed Apr. 29, 1992) and PCT/US93/04145 (filed Apr. 28, 1993), the disclosures of which are incorporated herein by reference.

In one group of preferred embodiments, a library of arene compounds is prepared using bead-based synthesis. In brief, beads are suitably modified with a connecting group, for example, aminoalkyltriethoxysilane, to provide beads having amino groups as synthesis initiation sites. Traceless linkers are attached to the amino groups to provide derivatized beads having a general formula:

in which $S^0$ is the solid support and L is a combination of connecting group (aminoalkylsilane) and traceless linker.

The libraries of the present invention can be used for development of new therapeutic agents as well as for the evaluation of existing therapeutic candidates. For example, libraries comprising a plurality of therapeutic candidates can be prepared on beads as described above and evaluated as a single bead-based candidate or as pooled beads. Additionally, the candidates can be cleaved from the beads and evaluated individually or as a solution of multiple candidates. Evaluation of the beads or cleaved therapeutic candidates is typically carried out to determine the efficacy of each candidate against a variety of diseases states associated with a particular receptor activity.

Alternatively, a library of ligands can be prepared in which each ligand has a known affinity for a selected receptor. Following preparation of the library, a solution of labeled receptor is incubated with the library to attach the receptor to the various ligands. A displacement assay, using drug candidates can then be carried out by incubating the library with the drug candidate and determining the extent to which the drug candidate displaces the receptor from the ligands.

In preferred embodiments, the libraries are synthesized on beads in a number of containers, and the beads are then exposed to a receptor of interest. More preferably, the modified arene compounds (or target arenes) which are prepared by the above methods are removed from the bead supports and screened in solution. In this group of embodiments, the compounds optionally are tagged using methods described in co-pending application Ser. No. 08/577,203, filed Dec. 22, 1995 and incorporated herein by reference. For those embodiments in which the modified arene compound is not removed from the bead, the receptor is preferably fluorescently or radioactively labelled. Thereafter, one or more beads are identified that exhibit significant levels of, for example, fluorescence using one of a variety of techniques. For example, in one embodiment, mechanical separation under a microscope is utilized. The identity of the molecule on the surface of such separated beads is then identified using, for example, NMR, mass spectrometry, and decoding of the associated tags, or the like. In another embodiment, automated sorting (i.e., fluorescence activated cell sorting) can be used to separate beads (bearing probes) which bind to receptors from those which do not bind.

The foregoing description is offered primarily for illustration and not as a limitation. It will be readily apparent to those of ordinary skill in the art that the operating conditions, materials, procedural steps and other parameters of the system described herein may be further modified or substituted in various ways without departing from the spirit and scope of the invention.

Accordingly, the scope of the invention should, therefore, be determined not with reference to the above description, but instead should be determined with reference to the appended claims along with their full scope of equivalents.

What is claimed is:

1. A composition for the solid phase synthesis of organic compounds, said composition having the formula:

wherein, $S^0$ is a solid support;

B is a connecting group;

M is a transition metal selected from the group consisting of ruthenium, chromium, iron, molybdenum and manganese;

each L is independently a transition metal ligand;

n is an integer of from 1 to 4, said integer begin selected to provide M with a sufficient number of ligands to fill the available valences; and

$X^-$ is a counterion.

2. A, composition in accordance with claim 1, wherein each of said transition metal ligands is $NCCH_3$.

3. A composition in accordance with claim 1, wherein M is ruthenium, each of said transition metal ligands is $NCCH_3$, and n is 3.

4. A composition in accordance with claim 1, wherein $S^0$ is a glass bead or polyacrylate support, M is ruthenium, each of said transition metal ligands is $NCCH_3$, and n is 3.

5. A composition comprising an arene compound on a solid support, said composition having the formula:

wherein, $S^0$ is a solid support;

B is a connecting group;

M is a transition metal selected from the group consisting of ruthenium, chromium, iron, molybdenum and manganese;

Ar is an arene compound attached to M through an $\eta^6$-arene $\pi$-complex and

$X^-$ is a counterion.

6. A composition in accordance with claim 5, wherein M is selected from the group consisting of ruthenium, chromium, molybdenum and iron.

7. A composition in accordance with claim 5, wherein M is ruthenium.

8. A composition in accordance with claim 5, wherein said solid support is selected from the group consisting of CPG, PEG resins, polystyrene and polyacrylate resins.

9. A library comprising a plurality of members of arene compounds on a solid support, each member independently having the formula:

wherein $S^0$ is a solid support;

B is a connecting group;

M is a transition metal selected from the group consisting of ruthenium, chromium, iron, molybdenum and manganese;

Ar is an arene compound attached to M through an $\eta^6$-arene $\pi$-complex; and $X^-$ is a counterion.

10. A library in accordance with claim 9, wherein M is selected from the group consisting of ruthenium, chromium, molybdenum and iron.

11. A library in accordance with claim 9, wherein $S^0$ is selected from the group consisting of CPG, PEG resin, polystyrene and polyacrylate.

12. A library in accordance with claim 9 having of from 10 to 100,000 members.

13. A composition for the solid phase synthesis of organic compounds, said composition having the formula:

$$S^0\text{—}B\text{—}ED\text{—}M\text{—}(L)_n{}^+X^-$$

wherein, $S^0$ is a solid support;

B is a connecting group;

ED is an electron donating ligand selected from the group consisting of dienyl ligands, cyclopentadienyl ligands and phosphorus-containing ligands;

M is a transition metal selected from the group consisting of ruthenium, chromium, iron, molybdenum and manganese;

each L is independently a transition metal ligand;

n is an integer of from 1 to 4, said integer being selected to provide M with a sufficient number of ligands to fill the available valences; and $X^-$ is a counterion.

14. A composition in accordance with claim 13, wherein ED is a phosphorus-containing ligand, M is iron or molybdenum and at least one L is a diene or allyl group.

15. A composition in accordance with claim 13, wherein ED is a phosphorus-containing ligand, M is iron or molybdenum, one of said L ligands is a diene or allyl group, and the remaining L ligands are carbon monoxide ligands.

* * * * *